United States Patent [19]

Kalat

[11] 4,110,427

[45] Aug. 29, 1978

[54] POWDERED SOLID AEROSOL COMPOSITION AND METHOD OF MANUFACTURE

[75] Inventor: Edwin F. Kalat, Thomaston, Conn.

[73] Assignee: The Risdon Manufacturing Company, Naugatuck, Conn.

[21] Appl. No.: 677,075

[22] Filed: Apr. 14, 1976

[51] Int. Cl.$^2$ .............................................. A61K 9/14
[52] U.S. Cl. ................................... 424/46; 252/305; 424/66; 424/318; 424/361
[58] Field of Search ....................... 424/46, 47, 68, 66, 424/67

[56] References Cited

U.S. PATENT DOCUMENTS

| | | | |
|---|---|---|---|
| 2,269,529 | 1/1942 | Goldsmith | 424/365 X |
| 3,088,874 | 5/1963 | Geary et al. | 424/47 |
| 3,479,297 | 11/1969 | Rutzen et al. | 424/76 |
| 3,903,258 | 9/1975 | Siegal | 424/358 |

FOREIGN PATENT DOCUMENTS 864,527   2/1971   Canada ........................... 424/47

*Primary Examiner*—Dale R. Ore
*Attorney, Agent, or Firm*—St. Onge, Steward, Johnston, Reens & Noe

[57] ABSTRACT

A water-based composition, which includes a water and carrier liquid insoluble powdered solid and is easily dispensed as a spray from a container without clogging the container components, is characterized by having at least 15 and as much as 50 percent powder by weight of the composition. The composition further includes from 20 to 70 percent of water by weight and from 25 to 50 percent of an anhydrous, hydrophobic carrier liquid by weight which may entirely or only in part be an aerosol propellant. An emulsifier is added to create a water-and-carrier liquid emulsion in which the powdered solid is dispersed.

13 Claims, No Drawings

POWDERED SOLID AEROSOL COMPOSITION AND METHOD OF MANUFACTURE

BACKGROUND OF THE INVENTION

1. Field of the Invention

The present invention relates to a water-based composition which includes a powdered solid, carried to be dispensed from a pressurized aerosol container.

Aerosol containers are commonly used to dispense a wide variety of consumer products including household products such as pesticides, germicides, and liquid cleaners, and personal products such as deodorants, antiperspirants, and colognes. Such containers provide a convenient way for storing as well as for using products of this general type in the home or office. However, certain problems have been encountered in adapting conventional aerosol technology to dispense powdered solid products such as talcs, processed starches, pigments, silicas, powdered metals, clays and the like, which are essentially insoluble in commonly used aerosol propellants and in water. These products can only be dispensed in spray form as a solid particulate.

2. Description of the Prior Art

Most presently known compositions for carrying a powdered solid product to be dispensed from an aerosol container comprise up to 10 percent by weight of solid product, approximately 1 percent perfume, 1 percent emollient and approximately 90 percent aerosol propellant. Therefore, the amount of available product is obviously relatively small compared to other components.

Attempts to increase the amount of powdered solid product in the composition usually resulted in increased product agglomeration and compaction on standing to such a degree that normal agitation of the container would not redisperse the powder particles in their carrier. Moreover, in such cases, the container components and particularly the aerosol valve became clogged rendering the container useless. However, when the amount of powdered solid was kept at or below 10 percent by weight of the composition, these operating problems were minimized.

Yet other problems existed. For example, the propellant ordinarily used in amounts of up to 90 percent of the composition was a fluorocarbon such as fluorocarbon P-11, fluorocarbon P-12, fluorocarbon P-114 or any combination of the three. Hydrocarbon propellants, which may be more desirable in certain circumstances, were not used because they are flammable and can consequently be dangerous when employed in high concentrations.

More recently, other attempts have been made to increase the amount of powdered solid product contained in aerosol compositions. For example, U.S. Pat. No. 3,088,874 (Geary et al.) discloses a powdered aerosol system for dispensing a composition having a surfactant, a bulking agent, a non-polar liquid and a propellant combined in a certain ratio by volume. In this system, an active powder having particles of diameter of at least 15 microns can be dispensed in quantities of at least 15 percent by weight of the composition. The non-polar liquid is said to reduce the cohesive forces between the active powder particles and hence to reduce compaction to ease dispensing. Still, the compositions disclosed in the examples given in the Geary et al. Patent utilize aerosol propellant in the relatively high range of 53.2 to 68.1 percent by weight of the composition and utilize no water.

U.S. Pat. No. 2,959,325 (Beard), assigned to the assignee of the present invention, discloses a method and apparatus for dispensing dry particles. The composition which may be dispensed includes a liquid base and the powdered solid. Both components have nearly the same specific gravity in order to prevent agglomerative sedimentation of the solid. In this way, a relatively high percentage by weight of powdered solid may be included. However, the liquid, which is the propellant, is also contained in relatively large amounts.

Both the Geary et al. and Beard Patents, then, disclose aerosol compositions for dispensing a powdered solid product which also include large amounts of propellant. As noted above, the type of propellants that can be used are, therefore, limited largey to fluorocarbons. However, the yet undefined problem of atmospheric ozone reduction may render use of this category of fluorocarbon propelled products untenable in the future. The large amounts of propellant also increases the cost of the compositions.

The high concentration of propellant in these compositions produces a chilling feeling when sprayed on the skin caused by rapid evaporation of residual propellant. This effect is particularly undesirable when personal or cosmetic products are dispensed. Therefore, these compositions have certain drawbacks.

Other aerosol compositions are disclosed in U.S. Pat. Nos. 3,773,683 (Aubert); 3,568,394 (Margolis); and 2,968,628 (Reed).

SUMMARY OF THE INVENTION

It is an object of the present invention to provide a waterbased composition which includes relatively high concentrations of a powdered solid, that is insoluble in water and in typical hydrophobic, anhydrous carrier liquids, to be dispensed as a spray from a container. This composition, moreover, uses smaller amounts of carrier liquid, and, particularly in aerosol applications, smaller amounts of condensed aerosol propellant gases, than known compositions yet operates effectively.

It should be understood that the term "insoluble" is intended to mean essentially insoluble and that the term "anhydrous" is intended to mean essentially anhydrous.

In a preferred embodiment, to be described below in detail, the composition of the present invention includes a powdered solid that is carried to be dispensed from a pressurized aerosol container in amounts of at least 15 percent and up to 50 percent by weight of the composition. At most, this composition contains 50 percent by weight of an anhydrous carrier liquid or mixture of carrier liquids which may entirely or only in part be a condensed aerosol propellant gas. Therefore, the cost per aerosol unit is decreased by decreasing the amount of the carrier liquid, and in particular, of the propellant needed. Further, by lowering the concentration of propellant, hydrocarbon rather than fluorocarbon types may be used, thus, further lowering the cost per aerosol unit. It should be noted that the composition of the invention, may also be dispensed from non-pressurized containers such as finger-operated pump type packages. In such cases, the carrier liquid may comprise a paraffinic oil.

The composition also comprises a water base of 20 to 70 percent by weight of the composition. The anhydrous carrier liquid constitutes 10 to 50 percent by weight. Emulsifying agents are added to the composition in an amount ranging from 0.1 to 10.0 percent by weight to effect a strong water-and-carrier liquid emulsion in which the insoluble powdered solid is dispersed. Thus, the quantity of actual usable product is greatly increased over commonly available powdered solid aerosol compositions.

It has been found that when the composition having components in the above-noted amounts is dispensed from a container as a spray, the water is dispersed or adsorbed over the large surface area presented by the powdered solid. Therefore, the water evaporates rapidly from the composition which accordingly feels quite dry and is not at all runny or muddy. Moreover, since a water-and-carrier liquid emulsion is the carrier for the powdered solid, the adsorption of water about the powder particles yields two results: (1) It reduces the bulk of the powder, and (2) It prevents compaction and agglomeration of the powder which remains effectively suspended or dispersed in the emulsion. The reduction of the powder bulk makes possible the inclusion of powder in high concentrations and, therefore, further contributes to the dry feel of the composition when dispensed from the container.

In aerosol applications, because the concentration of propellant carrier liquid is greatly reduced, and further because the propellant is diluted with water, the aerosol package will not be dangerously flammable even if hydrocarbon propellants are used. Therefore, previous deterrents to use of hydrocarbon propellants are eliminated.

The emulsion in which the powdered solid is dispensed may be either of the water-in-carrier or carrier-in-water types. However, in practice, the water-in-carrier emulsion is more satisfactory for use in metal containers since it is non-corrosive.

The aerosol composition of the present invention may also include an emollient or oil in amounts ranging from 5 to 20 percent by weight to improve the feel of the product, if one of many personal products, when dispensed onto the skin. Further, it may also include a perfume for esthetic reasons in amounts up to 5 percent by weight. Accordingly, the present invention avoids many problems of the prior art and provides several additional advantages.

In accordance with the present invention, it is desirable that the components of the emulsion, namely, the water and carrier liquid be quickly removed from the powdered solid product after all are dispensed. As noted above, the water adsorbed about the dispensed powder evaporates rapidly to effect removal of the aqueous phase of the emulsion and thus promote the dry feeling of the spray. Similarly, to this end, it is desirable to use a reasonably volatile anhydrous carrier liquid. In aerosol applications, the conventional fluorocarbon aerosol propellants such as P-11, P-12, or P-114 and hydrocarbon propellants such as propane, butane, and isobutane are satisfactory. However, if the propellant is the sole carrier liquid in the composition the process of emulsifying the aqueous and anhydrous phases may be conducted only with certain difficulty under pressure or supercooled conditions or both in suitable vessels. The emulsion is then introduced under the same conditions into individual aerosol containers. Alternatively, the emulsion may be formed in situ in the aerosol containers themselves.

The complexity of either of the processes described above may be avoided by using an intermediate or secondary anhydrous carrier liquid, miscible in the propellant, having volatility lower than the propellant, yet adequate to be removed from the product within a reasonable time under normal ambient atmospheric conditions when dispensed. To do so, the water and intermediate carrier are first emulsified without using enclosed pressure vessels or supercooling. The powdered solid is then dispersed in this concentrated initial emulsion and the entire dispersion is introduced into the container before a valve assembly is crimped thereto. The propellant component of the anhydrous phase can then be introduced into the container through the valve or in any one of other well known methods.

Volatilization of the carrier is not the only mechanism available for removing or separating it from the emulsion in order to leave the powdered solid as a residue when dispensed. For example, a separation is possible by selecting an emulsion which is stable under the conditions existing in a closed, and especially a pressurized, container yet which is unstable under exposed conditions of normal use. Even if the anhydrous carrier liquid is relatively non-volatile in such case, the phase separation occurring on break-down of the emulsion when exposed to atmosphere in conjunction with evaporation of the aqueous phase, leaves the powdered solid as the only residue. Accordingly, reference herein to anhydrous carrier liquids is not to be construed as being limited to those having good volatility, although this is many times preferred for practical reasons in aerosol applications.

In general, a wide selection of carrier liquids is available and will be determined by the end application of the powdered product. However, the carrier liquid should be anhydrous to form a strong emulsion with the water so that the powdered solid can be effectively dispersed without agglomeration and compaction on standing. The carrier should also be chemically inert with respect to the powder. Other considerations in the selection of the carrier include such things as toxicity, staining effect, odor, and, of course, cost. Suggested materials include liquid saturated aliphatic hydrocarbons of the paraffinic series such as hexane, pentane and other homologs; unsaturated aliphatic compounds such as pentene, hexene, etc.; aromatic compounds such as benzene or homologs thereof; esters, including isopropyl myristate previously used simply for slurrying purposes, ethyl acetate, etc.; halogenated hydrocarbons, including the usual aerosol propellants already mentioned; even such things as light mineral oil, carbon tetrachloride, etc. are possibilities for some purposes, though not of course where volatility, toxicity, odor, etc. are important considerations. As noted above, though, in aerosol applications hydrocarbons such as butane, isobutane, and propane are considered desirable because of their relatively low cost and because they avoid the potential objections to fluorocarbons. Of course, also as noted above, the objection to use of concentrated hydrocarbons due to their flammability is eliminated by the addition of the aqueous phase in the composition of the invention.

The invention may be best illustrated by the following typical formulations of water-based compositions which contained a powdered solid dispersed in a water-and-carrier liquid emulsion.

EXAMPLE 1

| Component | Amount (Percent by weight) |
| --- | --- |
| Low micron talc | 30.0 |
| "Emcol 14" (polyglcerol oleate) | 1.3 |
| "Isopar E" (Isoparaffinic oil) | 10.0 |

-continued

| Component | Amount (Percent by weight) |
|---|---|
| Dipropylene glycol | 2.0 |
| Perfume | .5 |
| Deionized Water | 26.2 |
| Propellant: Propane | 4.8 |
| Butane | 25.2 |
| | 100.0 |

The powdered solid in this formulation is low micron talc, that is, talc having particles no larger than 100 microns. It is useful in many applications as a personal product and can be the main component of such products as baby powder.

The polyglycerol oleate is the emulsifying agent in this system. The particular product chosen, identified by the trademark "Emcol 14" of the Whitco Chemical Corporation, has been found well suited to the present application. It produces a strong water-in-propellant emulsion and further is a good corrosion inhibitor, a feature particularly useful when the composition is packaged in a metal container.

The isoparaffinic oil, such as "Isopar E" available from Humble Oil and Refining Co., is the secondary anhydrous carrier liquid. It is used to form the initial or concentrated emulsion containing all of the components with the exception of the propellant or mixture of propellants. The aerosol package is then prepared in the manner described above by introducing the concentrated emulsion in a measured amount into an individual aerosol container before the valve assembly is crimped to the container. The propellant is then introduced by conventional methods through the valve.

"Isopar E" has a boiling temperature range, under ambient atmospheric conditions, of approximately 240° to 290° F. It has very low toxicity, a pleasant low impact odor, good viscosity, extremely low water solubility (about 98 ppm water in hydrocarbon and 7 ppm hydrocarbon in water at room temperature), but good solubility in aerosol propellants and a number of other nonaqueous liquids. It is completely volatilized in about 300 to 350 seconds when exposed under ambient atmospheric conditions. It is also very low in non-isoparaffinic hydrocarbon and other impurities. For these reasons, it has been found to be well suited for use in preparing aerosol formulations in accordance with the present invention. It can be used in varying amounts. However, it is best used in the minimum amount which will still provide a stable, strong, water-in-oil emulsion in the final composition.

The dipropylene glycol also forms a part of the anhydrous carrier liquid phase with the isoparaffinic oil and propellant. It, like "Isopar E," is an emollient and is added to improve the feel of the composition when dispensed onto the skin.

The perfume is added for esthetic reasons and may be increased or eliminated as desired.

Since the water and propellant constitute approximately the same proportions of the composition, it is practical in most cases to substitute pure hydrocarbon types for the fluorocarbons and other halogenated hydrocarbon types. The combination of propane and isobutane in Example 1 has been found to be particularly satisfactory in substantially lowering the unit cost below that possible when most fluorocarbon propellants are used. However, it is still possible to use halogenated hydrocarbon propellants either alone or in combination with the hydrocarbon propellants.

Water is added in amounts as large as possible to reduce the cost and particularly with hydrocarbon propellants, to reduce the flammability of the product. A composition having up to 70 percent has been found to be acceptable.

Some of the variations noted with respect to Example 1 as well as noted earlier in this specification may be illustrated with reference to the following examples.

EXAMPLE 2

| Component | Amount (Percent by weight) |
|---|---|
| Dry flow starch (Non-water soluble processed starch) | 29.09 |
| "Emcol 14" (Polyglycerol oleate) | .91 |
| "Isopar E" (isoparaffinic oil) | 9.09 |
| Deionized water | 30.91 |
| Propellant (Isobutane) | 30.00 |
| | 100.00 |

Example 2 uses a single secondary anhydrous carrier liquid, namely "Isopar E," and eliminates the use of dipropylene glycol. Dry flow starch has been substituted for the talc. However, the dispenser package operates equally well with either starch or talc.

EXAMPLE 3

| Component | Amount (Percent by weight) |
|---|---|
| Dry flow starch | 16.0 |
| Talc | 8.0 |
| Isopropyl myristate | 1.0 |
| "Isopar H" (light oil) | 9.0 |
| "Emcol 14" (polyglycerol oleate) | 1.5 |
| Water | 34.5 |
| Propellant (Isobutane) | 30.0 |
| | 100.0 |

The composition of Example 3 includes a combination of dry powdered solids namely, dry flow starch and talc. The isopropyl myristate and "Isopar H" form the secondary carrier liquid for initial preparation of the concentrated emulsion.

EXAMPLE 4

| Component | Amount (Percent by weight) |
|---|---|
| Zirconium oxide | 5.0 |
| Talc | 30.0 |
| Undecylenic acid | 3.0 |
| "Emcol 511" (modified alkanolamide) | 1.3 |
| Water | 30.7 |
| Propellant: Propane | 4.8 |
| Isobutane | 25.2 |
| | 100.0 |

The formulation set forth in Example 4 is for a foot powder. Specifically, the undecylenic acid is a medicament commonly used in such products. The powdered solid talc and zirconium oxide form a carrier for the medicament.

The modified alkanolanide, "Emcol 511," is the emulsifier. It has characteristics similar to "Emcol 14" and is obtained from the same supplier.

EXAMPLE 5

| Component | Amount (Percent by weight) |
|---|---|
| Zinc oxide | 20.0 |
| Dry flow starch | 10.0 |

-continued

| Component | Amount (Percent by weight) |
| --- | --- |
| Span 80 (sorbitan monooleate) | 2.0 |
| Light mineral oil | 10.0 |
| Deionized water | 23.0 |
| Propellant (Isobutane) | 35.0 |
| | 100.0 |

The composition in Example 5 also includes a combination of dry powdered solids, namely zinc oxide and dry flow starch. "Span 80," a sorbitan monooleate manufactured by Atlas Chemical Industries, is the emulsifier and creates a strong water-and-oil emulsion. Further, it is a good corrosion inhibitor. Light mineral oil forms the remainder of the oil phase for initial emulsifying stages in the production process.

EXAMPLE 6

| Component | Amount (Percent by weight) |
| --- | --- |
| Low micron talc | 40.0 |
| "Isopar H" (isoparaffinic oil) | 8.0 |
| "Emcol 14" (polyglycerol oleate) | 1.3 |
| Propylene glycol | 2.0 |
| Perfume | .5 |
| Deionized water | 25.0 |
| Propellant (propane, iosbutane) | 23.2 |
| | 100.0 |

EXAMPLE 7

| Component | Amount (Percent by weight) |
| --- | --- |
| Low micron talc | 50.0 |
| "Emcol 14" (polyglycerol oleate) | 1.3 |
| Propylene glycol | 1.0 |
| Light mineral oil | 8.0 |
| Deionized water | 19.2 |
| Perfume | .5 |
| Propellant: Isobutane | 16.8 |
| Propane | 3.2 |
| | 100.0 |

Examples 6 and 7 demonstrate that extremely high concentrations of dry powdered solids may be included in the composition of the present invention yet each of these compositions was successfully dispensed from an aerosol container.

EXAMPLE 8

| Component | Amount (Percent by weight) |
| --- | --- |
| Dry flow starch | 25.0 |
| "Crodesta"(sucrose monester) F-10 | 2.0 |
| "Isopar E" (isoparaffinic oil) | 8.0 |
| Perfume | 1.0 |
| Deionized water | 24.0 |
| Isobutane | 40.0 |
| | 100.0 |

In each of the above examples it has been demonstrated that by effecting a strong water-and-carrier emulsion, the powdered solid will nearly completely remain suspended in the composition. Agglomeration and compaction upon standing is prevented. Further, the powder may be dispersed through the composition with a minimum amount of aggitation. Thus, from the examples given above, it has been concluded that the composition should contain from 20 to 70 percent water, from 15 to 50 percent powdered solid, up to 20 percent emollients, from 25 to 50 percent carrier liquid, and from 0.1 to 10 percent emulsifier. Within these ranges, the composition may be easily dispensed from a conventional aerosol container to provide the consumer with a large amount of useable product as a proportion of the remaining components of the composition in a convenient package.

It has also been found that it may be desirable to incorporate a vapor tap aerosol valve in the aerosol container in such applications, to further insure that no container component clogging results.

Although specific examples of the present invention have been disclosed above in detail, it is to be understood that this is for purposes of illustration. Modifications may be made to the described aerosol compositions for dispensing a insoluble powdered solid by those skilled in the art in order to adapt these compositions to particular applications.

What is claimed is:

1. A water-based composition for carrying a powdered particulate solid, which is insoluble in both water and a carrier liquid, to be dispensed from a pressurized aerosol container as a spray, said composition comprising:

A. at least 20 percent water measured by the weight of the composition;

B. at least 15 percent powdered particulate solid, measured by the weight of the composition;

C. an anhydrous carrier liquid including a condensed aerosol hydrocarbon propellant gas that constitutes at most 50 percent of the composition measured by the weight thereof; and D. an emulsifying agent for forming an emulsion of said water and said carrier liquid in which the powdered particulate solid particles are dispersed.

2. The water-based composition for carrying a powdered solid, which is insoluble in water and a carrier liquid, to be dispensed from a pressurized aerosol container, as claimed in Claim 1 wherein said carrier liquid is in part a condensed aerosol propellant gas.

3. The water-based composition for carrying a powdered solid, which is insoluble in water and a carrier liquid, to be dispensed from a pressurized aerosol container, as claimed in claim 1 wherein said water is deionized.

4. The water-based composition for carrying a powdered solid, which is insoluble in water and a carrier liquid, to be dispensed from a pressurized aerosol container, as claimed in claim 1 wherein said carrier liquid comprises:

1. a primary component in the form of a condensed aerosol propellant gas, and
2. a secondary component, miscible in said primary component, for forming a concentrated emulsion with said water in which said powdered solid is dispersed prior to addition of said primary component.

5. The water-based composition for carrying a powdered solid, which is insoluble in water and a carrier liquid, to be dispensed from a pressurized aerosol container, as claimed in claim 1 wherein said carrier liquid is volalitizable under ambient atmospheric conditions and consequently evaporates from said composition when exposed to those conditions.

6. A water-based composition for carrying a powdered particulate solid which is insoluble in both water and a carrier liquid, to be dispensed from a pressurized aerosol container, said composition comprising:

A. between 20 and 70 percent water measured by the weight of the composition;
B. between 15 and 50 percent powdered particulate solid measured by weight of the composition;
C. a carrier liquid including a condensed hydrocarbon aerosol propellant gas that comprises at most 50 percent of the composition measured by weight; and
D. an emulsifying agent for forming an emulsion of said water and carrier liquid in which the powdered particulate solid particles are dispersed.

7. The water-based composition for carrying a powdered solid, which is insoluble in water and a carrier liquid, to be dispensed from a pressurized aerosol container, as claimed in claim 6 wherein said carrier liquid further includes a secondary component, miscible with said condensed propellant gas, for forming a concentrated emulsion with said water in which said powdered solid is dispersed prior to addition of said condensed propellant gas.

8. The water-based composition for carrying a powdered solid, which is insoluble in water and a carrier liquid, to be dispensed from a pressurized aerosol container, as claimed in claim 6, further comprising a perfume in an amount up to 2 percent by weight of the composition.

9. A water-based composition for carrying a powdered particulate solid, which is insoluble in water and a carrier liquid, to be dispensed from a pressurized aerosol container, said composition comprising:
A. from 20 to 70 percent water;
B. from 15 to 50 percent powdered particulate solid;
C. from 5 to 20 percent of an emollient;
D. from 25 to 40 percent of a hydrocarbon aerosol propellant;
E. from 0.1 to 10.0 percent of an emulsifier for forming an emulsion of said water and said propellant in which the powdered particulate solid particles are dispersed; the percentages of each composition component being measured by the total weight of the composition.

10. A method of preparing a waterbased composition for carrying a powdered solid which is insoluble in water and a carrier liquid to be dispensed from a pressurized aerosol container, said method comprising the steps of:

A. emulsifying one of a water component, and an anhydrous carrier liquid component in the other of the components, said water component comprising at least 20 percent of the composition measured by weight thereof, said carrier liquid component comprising at most 50 percent of the composition measured by the weight thereof and including a condensed hydrocarbon aerosol propellent gas; and
B. dispersing at least 15 percent powdered particulate solid by weight of the composition in the water and carrier liquid emulsion.

11. A method of preparing a water-based composition for carrying a powdered solid which is insoluble in water and a carrier liquid and for packaging the composition in an aerosol container, said method comprising the steps of:
A. emulsifying one of a water component and a secondary component of an anhydrous carrier liquid in the other of the components to form an initial emulsion;
B. dispersing at least 15 percent powdered solid by weight of the entire composition in the initial emulsion;
C. introducing the powdered solid dispersed in the initial emulsion into the aerosol container; and
D. adding a primary carrier liquid component in the form of an anhydrous condensed hydrocarbon aerosol propellant gas, miscible with the secondary carrier liquid component, to the initial emulsion in the aerosol container to form a final emulsion in which the powdered solid is dispersed.

12. The water-based composition for carrying a powdered solid to be dispensed from a pressurized aerosol container as claimed in claim 1, wherein said carrier liquid comprises at most 50 percent of the composition measured by the weight thereof, and wherein said condensed aerosol propellant gas comprises at most 40 percent of the composition measured by the weight thereof.

13. The water-based composition for carrying a powdered solid to be dispensed from a pressurized aerosol container as claimed in claim 6, wherein said carrier liquid comprises at most 50 percent of the composition measured by the weight thereof, and wherein said condensed aerosol propellant gas comprises at most 40 percent of the composition measured by the weight thereof.

* * * * *